(12) United States Patent
Pimentel (10) Patent No.: US 9,997,057 B2
(45) Date of Patent: Jun. 12, 2018

(54) VEHICLE EMERGENCY SYSTEM

(71) Applicant: John Pimentel, Key West, FL (US)

(72) Inventor: John Pimentel, Key West, FL (US)

( * ) Notice: Subject to any disclaimer, the term of this patent is extended or adjusted under 35 U.S.C. 154(b) by 0 days. days.

(21) Appl. No.: 15/497,306

(22) Filed: Apr. 26, 2017

(65) Prior Publication Data
US 2017/0309159 A1 Oct. 26, 2017

Related U.S. Application Data

(60) Provisional application No. 62/327,759, filed on Apr. 26, 2016.

(51) Int. Cl.
| | |
|---|---|
| *G08B 25/10* | (2006.01) |
| *G08B 21/04* | (2006.01) |
| *G01N 33/00* | (2006.01) |
| *B60R 11/04* | (2006.01) |
| *G08B 21/12* | (2006.01) |
| *G01S 19/42* | (2010.01) |
| *G08B 25/08* | (2006.01) |

(52) U.S. Cl.
CPC .............. *G08B 25/10* (2013.01); *B60R 11/04* (2013.01); *G01N 33/004* (2013.01); *G01N 33/0063* (2013.01); *G08B 21/0469* (2013.01); *G08B 21/12* (2013.01); *G08B 25/08* (2013.01); *B60R 2300/80* (2013.01); *G01S 19/42* (2013.01)

(58) Field of Classification Search
CPC .... G08B 25/10; G08B 21/0469; G08B 21/12; G08B 21/04; B60R 11/04; B60R 2300/80; G01S 19/42; G01N 33/004; G01N 33/0063; G01N 33/00
USPC .............. 340/500, 501, 517, 539.15, 539.22, 340/539.27, 540, 568.1, 572.1, 573.1, 5.1, 340/5.7, 6.1
See application file for complete search history.

(56) References Cited

U.S. PATENT DOCUMENTS

| | | | |
|---|---|---|---|
| 5,311,197 A * | 5/1994 | Sorden ................. | B60R 25/102 342/357.31 |
| 2006/0290518 A1* | 12/2006 | Bingle ................... | E05B 83/26 340/573.1 |
| 2015/0002672 A1* | 1/2015 | Hayakawa ............... | B60R 1/00 348/148 |
| 2017/0182939 A1* | 6/2017 | Phatak .................. | G08B 21/02 |

* cited by examiner

*Primary Examiner* — Brian Wilson
(74) *Attorney, Agent, or Firm* — Gutwein Law; Greg N. Geiser (57) ABSTRACT

Described herein is an emergency system with rear camera and sensor to report emergencies and accidents that occur to the vehicle to which the system is installed. The device includes various sensors, detectors, and communication elements to signal a triggering condition to an emergency services provider.

17 Claims, 9 Drawing Sheets

VEHICLE EMERGENCY SYSTEM

CROSS REFERENCE TO RELATED APPLICATIONS

This application claims priority to U.S. Provisional Patent Application No. 62/327,759 filed 26 Apr. 2016 to the above named inventor, and is herein incorporated by reference in its entirety.

FEDERALLY SPONSORED RESEARCH OR DEVELOPMENT

Not Applicable

SEQUENCE LISTING, A TABLE, OR A COMPUTER PROGRAM

Not Applicable

FIELD OF THE INVENTION

The invention relates generally to an emergency system with rear camera and sensors to report emergencies and accidents that occur to the vehicle to which the system is installed.

BACKGROUND

Currently there are a number of solutions for vehicle safety. One of these solutions attempts to rely on airbags, but this solution fails to meet the needs of the market because airbags are only designed to protect passengers in the event of a collision. Another solution attempts to use currently available in vehicle road assistance services and devices, but this solutions is similarly unable to meet the needs of the market because they are required to be activated and operated by a user and are not capable of passively alerting authorities in the event of an internal emergency, such as child left alone in a hot car, or an external emergency, such as a vehicle crash.

SUMMARY OF THE INVENTION

The device apparatus of the present invention relates to a vehicle monitoring and alert system. The device is adapted for engagement with the existing vehicle electronic components and communication to various agencies in the event of a triggering action. The device is more generally an emergency vehicle alert and assistance device. The device will alert authorities in the event of a crash. Further, the device includes various temperature and monitoring sensors for life form detection within the vehicle during extreme temperature conditions, such as when a child is left alone in a vehicle that is dangerously hot or cold. Still further, the device includes sensors allowing for the detection of excess levels of carbon monoxide in a vehicle and communicative capability to automatically roll down the windows and cease operation of the engine. The device generally fills a need within the marketplace for an apparatus that is newly adapted technology in the form of a sensing and alert device to monitor internal and external vehicle conditions that can save lives.

The invention advantageously fills the aforementioned deficiencies by providing a safety system with rear camera and sensor to report emergencies and accidents that occur to the vehicle to which the system is installed, which provides for a contacting of emergency response immediately should there be an accident or unattended child in a hot or cold vehicle.

The device communicative capabilities will alert local authorities via 911 of imminent dangerous conditions to the vehicle passengers with a GPS location, vehicle description and license plate image.

The apparatus is installed in the front of the vehicle near the rear-view mirror. Sensors in the apparatus detect life forms in the vehicle and whether temperatures are either rising or dropping to dangerous levels for the occupants.

The apparatus' hidden sensor detects extreme temperatures, carbon monoxide, impacts, submersion in water, and airbag deployment.

The device can be adapted for various installation options including integration into existing automobiles through use by automakers and installed on the assembly line for new vehicles or be added to a vehicle as an aftermarket addition in the form of a device that can be purchased by a consumer and affixed to and coupled with the existing electronic components and systems of a vehicle.

Among other things, it is an advantage of the invention to provide a safety system with a rear camera and sensors to report emergencies and accidents that occur to the vehicle to which the system is installed that does not suffer from any of the problems or deficiencies associated with prior solutions.

It is still further an advantage of the invention that if carbon monoxide is detected, the windows of the car are automatically rolled down, the engine is turned off, and 911 is alerted of the situation. Additionally, in the event the system detects an occupied vehicle at a high temperature, the vehicle windows (if automatic) will be rolled down, the horn activated, and communication with applicable authorities initiated.

Still further, the apparatus has a camera installed on the back of the vehicle near the license plate. When 911 is alerted of a dangerous situation, the rear camera takes a photograph of the license plate and sends it to the 911 services, along with a GPS location and description of the vehicle.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

The following detailed description includes references to the accompanying drawings, which forms a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus. These terms are not meant to limit the elements that they describe, as the various elements may be oriented differently in various applications.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The invention is directed to be a safety system with a rear camera, sensors, and communicative elements to report emergencies and accidents that occur to the vehicle to which the device of the system is installed.

The invention is a new technology that can be installed in existing vehicles to alert various agencies and authorities through the existing emergency 911 system in the event of a life-threatening condition potentially within a vehicle or resulting from the operation of the vehicle. The device of the present invention is adapted to send a GPS signal location and license plate photograph of the license plate installed at the rear of the vehicle to provide the location and license plate number to 911 service operators or other emergency services personnel.

The sensors of the device are installed and adapted to provide an alert signal in the event a life form (child or pet) is left in a car that is too hot or too cold, a car crash occurs in which airbags are deployed, the car is rolled over, and/or submerged in water, and/or if carbon monoxide is detected in the vehicle.

Figure 1:
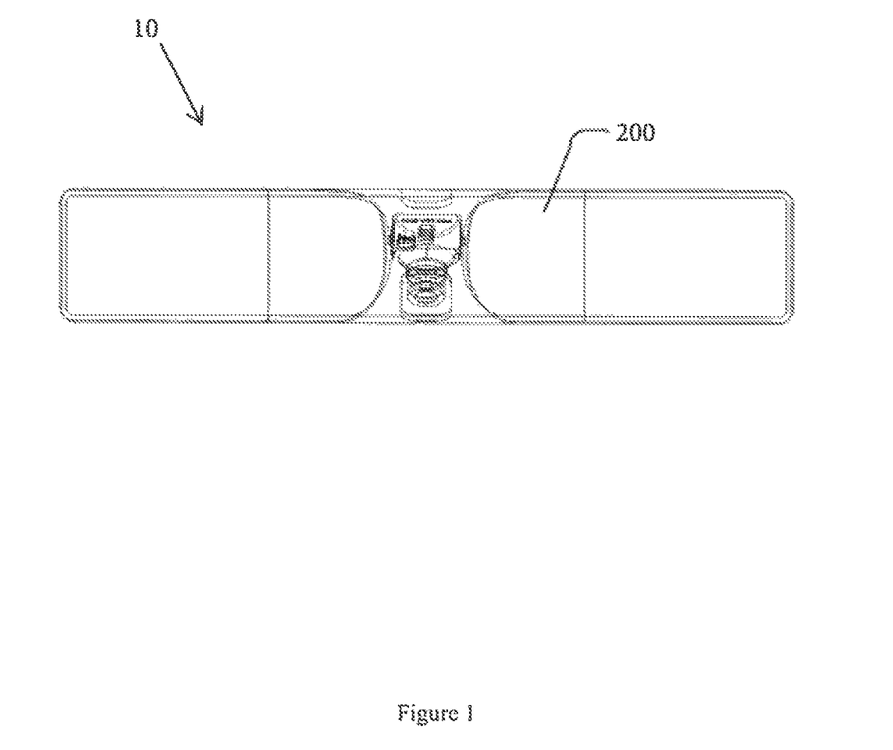
FIG. 1 shows the back view of the rear camera.
Figure 2:
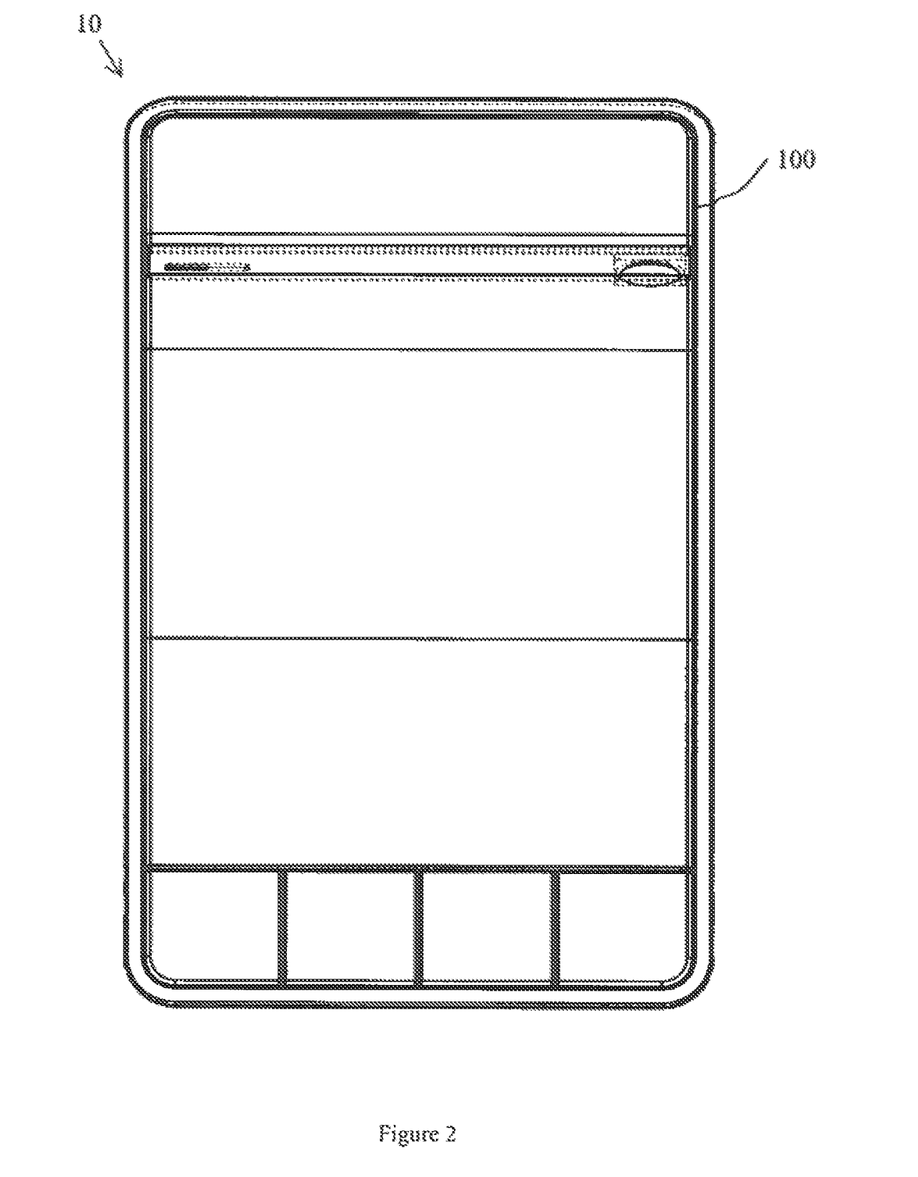
FIG. 2 shows the bottom of the device.
Figure 3:
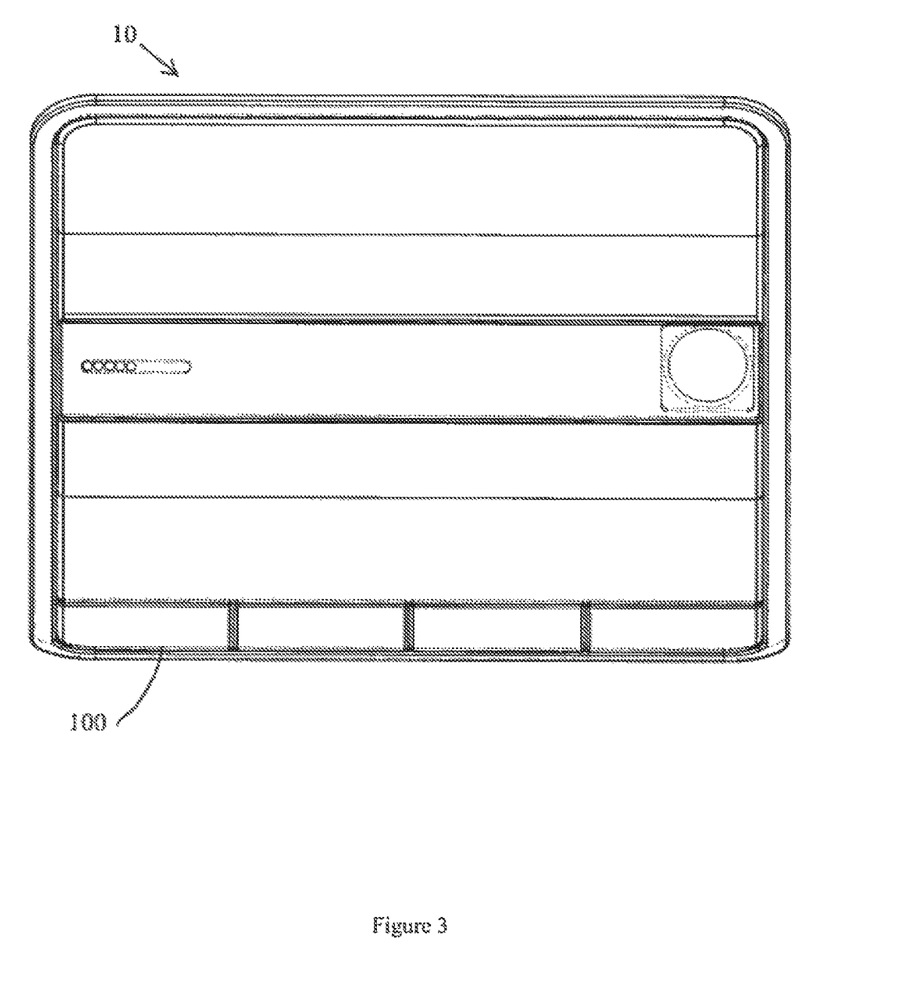
FIG. 3 shows the front of the device.
Figure 4:
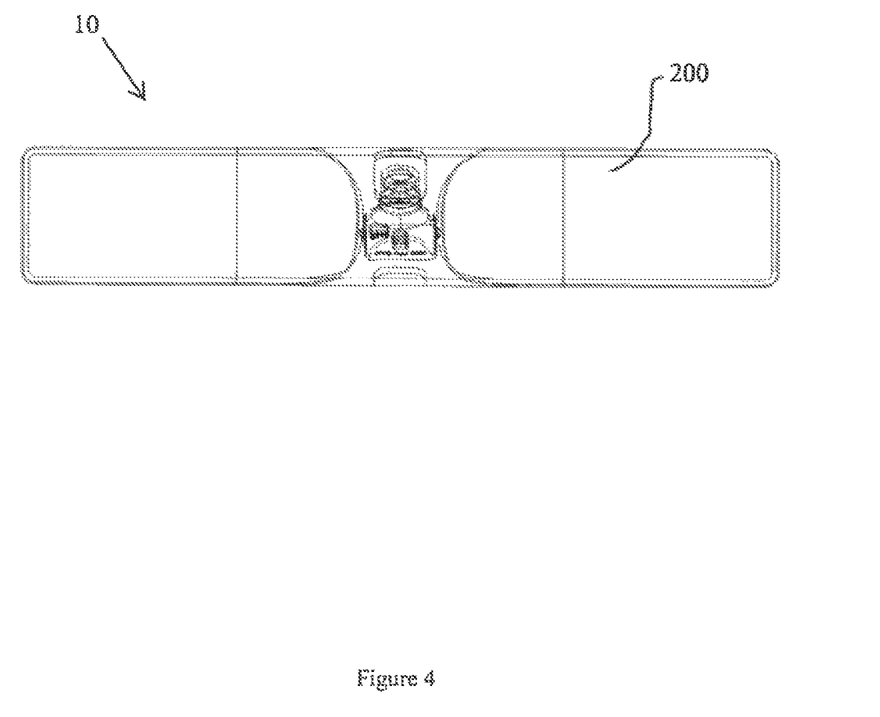
FIG. 4 shows the front view of the rear camera.
Figure 5:
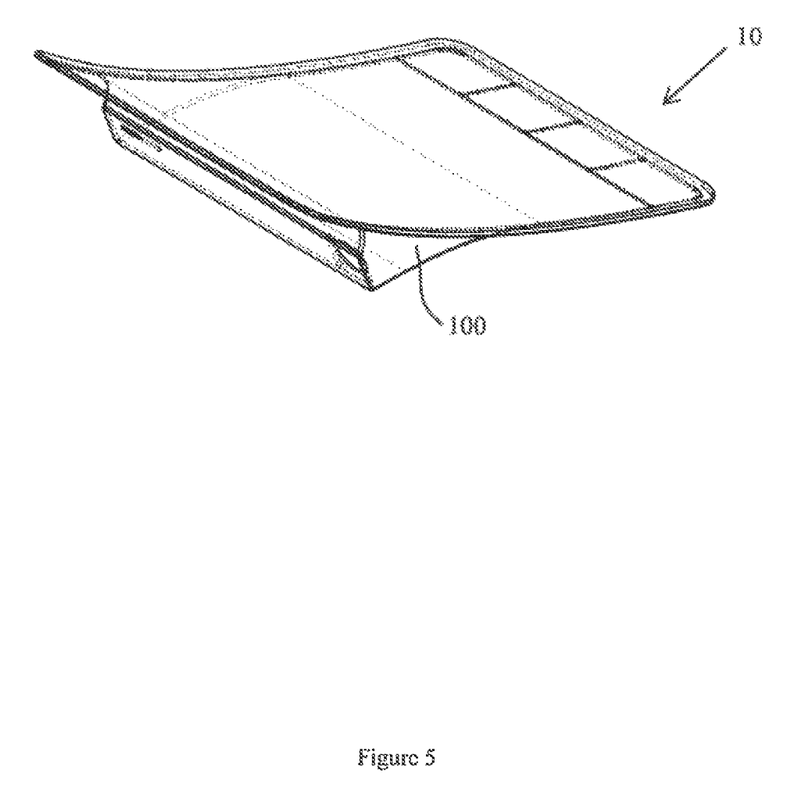
FIG. 5 shows an isometric view of the device.
Figure 6:
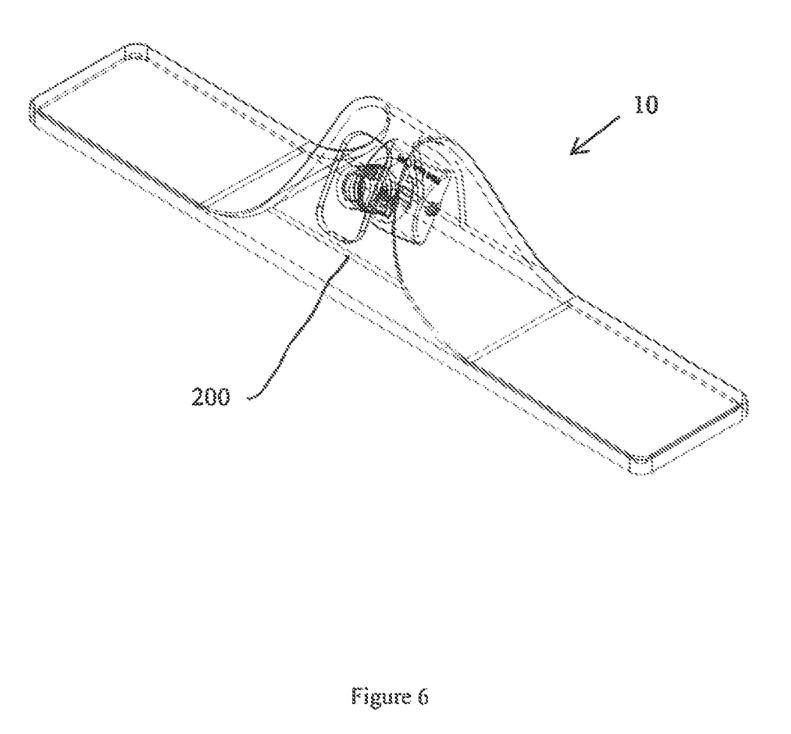
FIG. 6 shows an isometric view of the rear camera.
Figure 7:
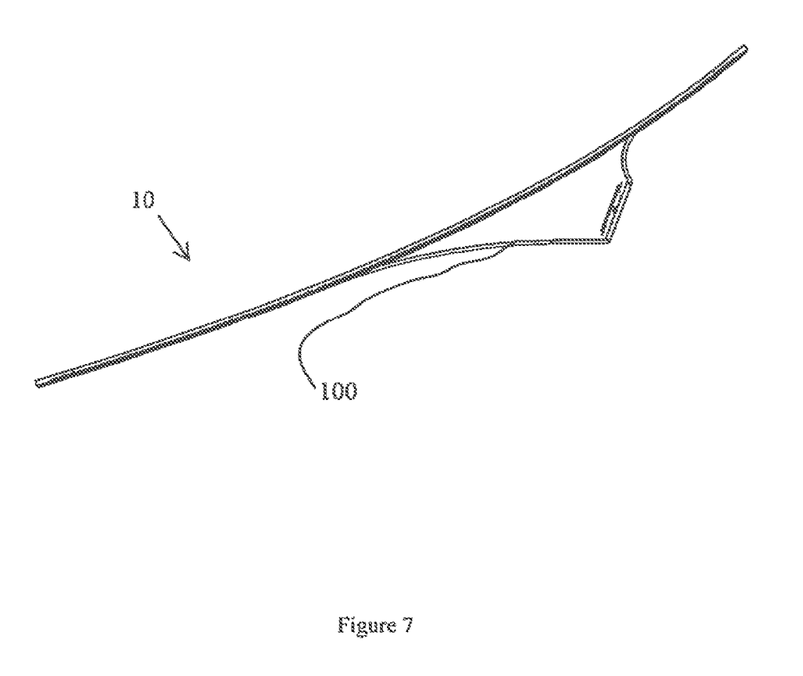
FIG. 7 shows a side view of the device.
Figure 8:
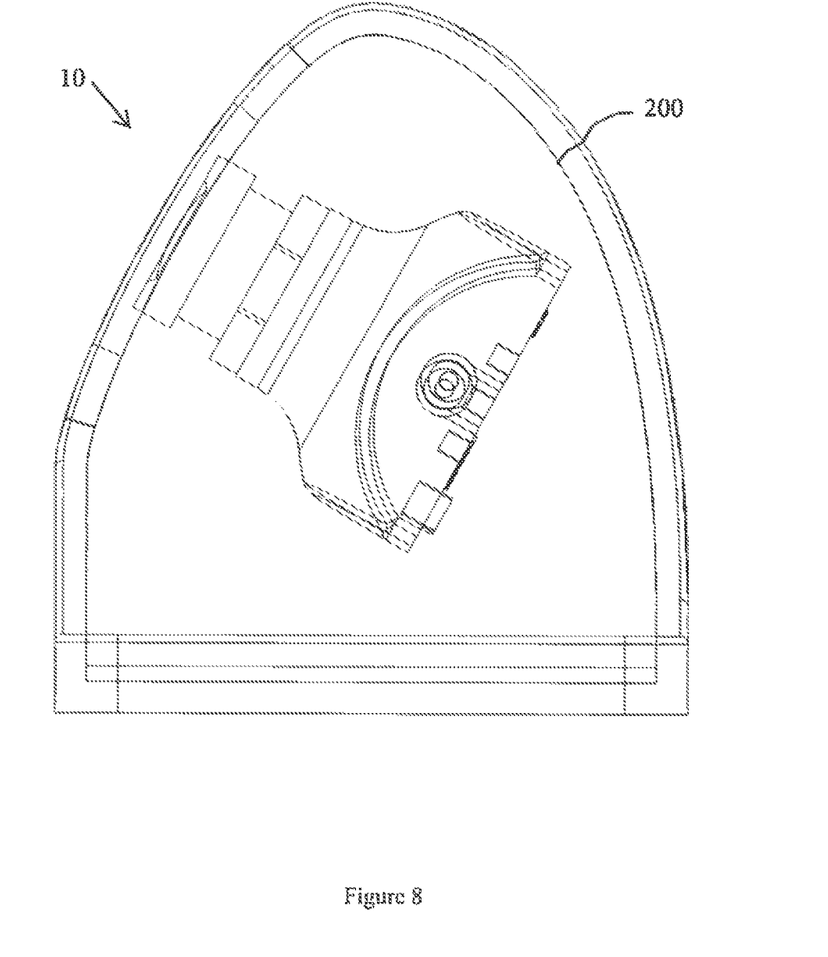
FIG. 8 shows the side view of the rear camera.
Figure 9:
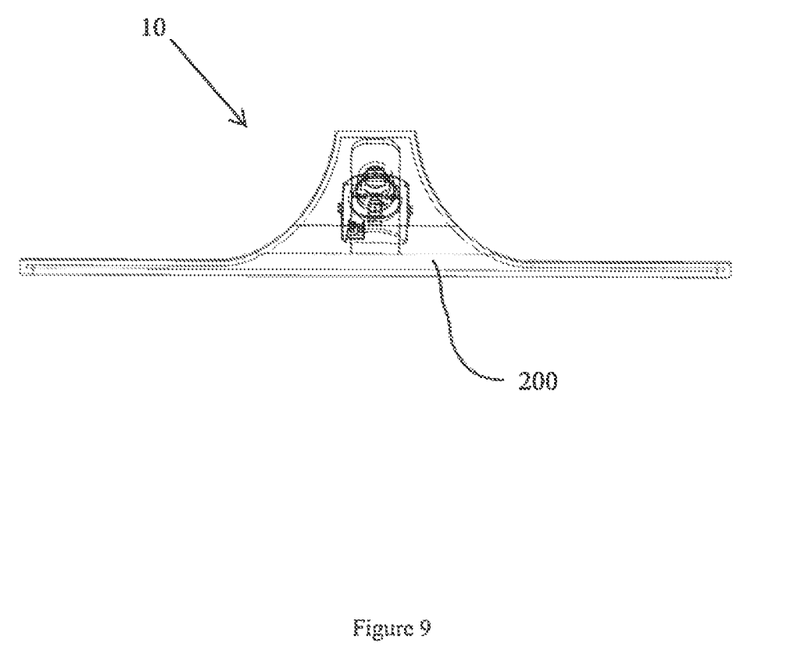
FIG. 9 shows the top view of the rear camera.

Referring to the figures, FIGS. 1-9 show various drawings of the features and visible elements of the safety system of the present invention, generally referred to as device 10. The device 10 is generally comprised of two separate components in a communicative coupling in the form of a sensor indicator console 100 and a rear camera 200. The sensor indicator console 100 is designed for placement near the interior rear view mirror of the vehicle when provided as an integrated accessory in new vehicles and as a stand-alone sensor indicator console 100 adapted for placement on the dashboard of existing vehicles. The sensor indicator console 100 is generally coupled to the vehicle electronics the device 10 is placed within, wherein the console 100 can be coupled to the existing vehicle wire harness through a wireless or wired connection. This coupling allows the device 10 to utilize both collected data through the device 10 sensors and internal and external vehicle data to effectuate a given response as directed by the internal components of the device 10.

Accordingly, the sensor console 100 internal electronic components include indicators and sensors to detect conditions including, but not limited to, temperature, occupancy, airbag deployment, moisture, oxygen deficiency, global positioning location, collision and avoidance sensors, impact sensors, roll over sensors, and various other sensors and detectors that may be related to other emergency conditions. These sensors within the device 10 and utilized by the device 10 may include, but not be limited to, thermometers, infrared sensors, carbon monoxide sensors/detectors, pressure sensors, heat sensors, accelerometers, and other now known or unknown sensors and detectors that may indicate an emergency condition.

The sensor console 100 includes communicative capability in the form of a signal generator and transmitter adapted to alert emergency services in the event of a detected emergency. This signal generator and transmitter may include, but not be limited to, cellular, radio, or wireless transmission and receipt to a given emergency services provider, such as, but not limited to, 911 emergency dispatch operators.

Upon detection of a triggering event, the device 10 various electronic components will utilize the rear camera 200 to capture an image of the rear license plate to provide this image to emergency services for use in aiding and resolving the emergency situation. The image of the license plate as captured by the camera 200 can be transmitted through the electronic components of the device 10 and provided to various authorities and emergency responders to aid in the resolution of the triggering condition.

Additionally, the console 100 and device 10 coupled communication with vehicle systems allows for the active prevention and cessation of emergency situations based upon constant and passive monitoring by the systems of the device 10, such as a cabin oxygen deficiency, infiltration of carbon monoxide, or the presence of a lifeform within a dangerously hot vehicle, wherein the vehicle windows may be rolled down, horn activated, and, in some instances, the vehicle engine stopped to correct the deficiency. The coupled communication with the vehicle systems allows the device 10 to take almost immediate action in the cessation of a potentially dangerous condition through the corresponding operation of the vehicle and its systems.

The device 10 sensors, may include a delay function, wherein the sensor is not triggered when an occupant first enters a vehicle that is currently within a condition that could regularly and potentially trigger an emergency situation, such as an extremely hot or extremely cold vehicle. Accordingly, the device 10 emergency condition will not be triggered during this delay period or until this delay period is expired. This prevents a triggering condition when an occupant first enters an extremely hot or cold vehicle.

The rear camera 200 of the device 10 is generally coupled to the sensor console and positioned on an exterior of the vehicle and aligned with the rear license plate. Accordingly, the rear camera 200 can be actively or passively triggered to capture an image of the rear license plate, wherein this image can be transmitted externally to an emergency services provider.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. A safety alert device and related system configured for placement into a vehicle, the safety alert device and related system comprising:
   a console member, the console member coupled electronically to the vehicle, the console member having:
      at least one temperature sensor, the temperature sensor configured to measure the temperature within the vehicle the console member is placed within;
      at least one sensor configured to detect the presence of an occupant within the vehicle; and
      a transmission/receiving device, the transmission/receiving device configured to send and receive communications from an emergency services provider; and
   a rear camera, the rear camera coupled to the console member, the rear camera placed on an exterior of the vehicle and positioned to capture an image of a rear license plate of the vehicle, wherein the image is transmitted to the emergency services provider for identification of the vehicle upon a triggering condition.

2. The safety alert device and related system as in claim 1, wherein the console member includes at least one oxygen sensor.

3. The safety alert device and related system as in claim 1, wherein the console member includes at least one carbon monoxide detector.

4. The safety alert device and related system as in claim 1, wherein the console member includes at least one global positioning satellite sensor (GPS).

5. The safety alert device and related system as in claim 1, wherein the safety alert device and related system and the transmission/receiving device is installed directly within the vehicle.

6. The safety alert device and related system as in claim 1, wherein the safety alert device and related system and the transmission/receiving device is provided as an after-market accessory configured for placement within the vehicle.

7. A safety alert device and related system configured for placement into a vehicle, the safety alert device and related system comprising:
   a console member, the console member coupled electronically to the vehicle, the console member having:
      at least one temperature sensor, the temperature sensor configured to measure the temperature within the vehicle the console member is placed within;
      at least one sensor configured to detect the presence of an occupant within the vehicle;
      at least one global positioning satellite (GPS) locator configured to provide a global positioning location for the vehicle; and
      a transmission/receiving device, the transmission/receiving device configured to send communications and receive communications from an emergency services provider; and
   a rear camera, the rear camera coupled to the console member, the rear camera placed on an exterior of the vehicle and positioned to capture an entire image of a rear license plate of the vehicle, wherein the image is transmitted to the emergency services provider for identification of the vehicle upon a triggering condition.

8. The safety alert device and related system as in claim 7, wherein the console member includes at least one oxygen sensor.

9. The safety alert device and related system as in claim 7, wherein the console member includes at least one carbon monoxide detector.

10. The safety alert device and related system as in claim 7, wherein the safety alert device and related system is installed directly within the vehicle.

11. The safety alert device and related system as in claim 7, wherein the safety alert device and related system is provided as an after-market accessory configured for placement within the vehicle.

12. A safety alert system for a vehicle, the system comprising:
   at least one sensor configured to detect the presence of an occupant of the vehicle;
   at least one sensor configured to detect temperature;
   at least one sensor configured to detect an amount of oxygen within the vehicle interior;
   at least one global positioning satellite (GPS) locator;
   a camera, the camera positioned at the rear of the vehicle and aligned with a rear license plate for capturing an image of the rear license plate; and a transmitter/receiver configured to transmit to and receive a signal from an emergency services provider, wherein a detected condition triggers a communication comprising the image to the emergency services provider for identification of the vehicle.

13. The safety alert system for the vehicle as in claim 12, wherein the detected condition is an occupant within the vehicle with the detected temperature being hot.

14. The safety alert system for the vehicle as in claim 12, wherein the detected condition is an occupant within the vehicle with the detected temperature being cold.

15. The safety alert system for the vehicle as in claim 12, wherein the detected condition is an accident.

16. The safety alert system for the vehicle as in claim 12, wherein the detected condition is an oxygen deficient environment within the vehicle interior.

17. The safety alert system for the vehicle as in claim 12, wherein the detected condition is the vehicle being submerged in water.

* * * * *